(12) United States Patent
Doron et al.

(10) Patent No.: US 11,433,184 B2
(45) Date of Patent: Sep. 6, 2022

(54) AUTOMATED SYSTEM FOR REGULATING A PATIENT'S BLOOD GLUCOSE LEVEL

(71) Applicant: Commissariat à l'Énergie Atomique et aux Énergies Alternatives, Paris (FR)

(72) Inventors: Eléonore Doron, La Tronche (FR); Sylvain Lachal, Saint Martin d'Heres (FR); Pierre Jallon, Corenc (FR)

(73) Assignee: Commissariat à l'Énergie Atomique et aux Énergies Alternatives, Paris (FR)

( * ) Notice: Subject to any disclaimer, the term of this patent is extended or adjusted under 35 U.S.C. 154(b) by 312 days.

(21) Appl. No.: 16/632,329

(22) PCT Filed: Jul. 13, 2018

(86) PCT No.: PCT/FR2018/051789
§ 371 (c)(1),
(2) Date: Jan. 17, 2020

(87) PCT Pub. No.: WO2019/016452
PCT Pub. Date: Jan. 24, 2019

(65) Prior Publication Data
US 2020/0197606 A1    Jun. 25, 2020

(30) Foreign Application Priority Data
Jul. 21, 2017   (FR) ..................... 1756960

(51) Int. Cl.
*A61M 5/172*   (2006.01)
*G16H 20/17*   (2018.01)
(Continued)

(52) U.S. Cl.
CPC .......... *A61M 5/1723* (2013.01); *G16H 20/17* (2018.01); *G16H 40/63* (2018.01); *G16H 50/50* (2018.01); *A61M 2230/201* (2013.01)

(58) Field of Classification Search
None
See application file for complete search history.

(56) References Cited

U.S. PATENT DOCUMENTS

| | | | |
|---|---|---|---|
| 2008/0183060 A1 | 7/2008 | Steil et al. | |
| 2014/0066884 A1* | 3/2014 | Keenan | A61M 5/172 |
| | | | 604/504 |

FOREIGN PATENT DOCUMENTS

| | | | |
|---|---|---|---|
| GB | 2 436 873 A | 10/2007 | |
| WO | WO-2007116226 A2 * | 10/2007 | ........ A61M 5/1723 |
| WO | WO 2010/025431 A1 | 3/2010 | |

OTHER PUBLICATIONS

International Search Report and Written Opinion for International Application No. PCT/FR2018/051789, dated Nov. 6, 2018.

(Continued)

*Primary Examiner* — Manuel A Mendez

(57) ABSTRACT

An automated system of regulation of a patient's blood glucose, including: a blood glucose sensor; an insulin injection device; and a processing and control unit capable of predicting, from a physiological model, the future evolution of the patient's blood glucose over a prediction period, and of controlling the insulin injection device by taking the prediction into account, wherein the processing and control unit is capable of: a) calibrating the physiological model, taking into account the blood glucose measured by the sensor during a past observation period; b) at the end of the calibration, calculating an indicator representative of the error between the blood glucose estimated from the model (Continued)

and the real blood glucose measured by the sensor; and c) adjusting the prediction period by taking into account the value of the indicator.

11 Claims, 2 Drawing Sheets

(51) Int. Cl.
*G16H 50/50* (2018.01)
*G16H 40/63* (2018.01)

(56) References Cited

OTHER PUBLICATIONS

Jallon et al., Personalization of a compartmental physiological model for an artificial pancreas through integration of patent's state estimation. IEEE 2017 39th Annual International Conference of the IEEE Engineering in Medicine and Biology Society (EMBC). Jul. 11, 2017:1453-6.

Hovorka et al., Blood glucose control by a model predictive control algorithm with variable sampling rate versus a routine glucose management protocol in cardiac surgery patients: a ramdomized controlled trial. Journal of Clinical Endocrinology & Metabolism. 2007;92(8):2960-4.

Hovorka et al., Nonlinear model predictive control of glucose concentration in subjects with type 1 diabetes. Physiological Measurement. 2004;25(4):905-20.

Kopecky et al., The use of continuous glucose monitoring combined with computer-based eMPC algorithm for tight glucose control in cardiosurgical ICU. Biomed Research International. 2013;2013:1-8.

Oviedo et al., A review of personalized blood glucose prediction strategies for T1DM patients: personalized blood glucose prediction strategies for T1D patients. International Journal for Numerical Methods in Biomedical Engineering. 2017;33(6):e2833.

\* cited by examiner

AUTOMATED SYSTEM FOR REGULATING A PATIENT'S BLOOD GLUCOSE LEVEL

The present patent application claims the priority benefit of French patent application FR17/56960 which is herein incorporated by reference.

BACKGROUND

The present application relates to the field of automated blood glucose regulation systems, also called artificial pancreases.

DISCUSSION OF THE RELATED ART

An artificial pancreas is a system enabling to automatically regulate the insulin intakes of a diabetic patient based on his/her blood glucose history, on his/her meal history, on his/her insulin injection history.

MPC-type regulation systems or model-based predictive control systems, where the regulation of the delivered insulin dose takes into account a prediction of the future evolution of the patient's blood glucose, obtained from a physiological model describing the assimilation of insulin by the patient's body and its impact on the patient's blood glucose, are here more particularly considered.

It would be desirable to be able to improve the performance of model-based predictive control artificial pancreases and, more particularly, to be able to improve the quality of the prediction of the patient's future blood glucose, to be able to control with a better relevance insulin intakes and to limit risks of placing the patient in a hyperglycemia or hypoglycemia situation.

SUMMARY

Thus, an embodiment provides an automated system of regulation of a patient's blood glucose, comprising:
 a blood glucose sensor;
 an insulin injection device; and
 a processing and control unit,
 wherein the processing and control unit is capable of:
 a) implementing, taking into account the blood glucose measured by the sensor during a past observation period, a step of automated calibration of a physiological model capable of predicting the evolution of the patient's blood glucose;
 b) at the end of the calibration step, calculating at least one numerical indicator representative of the error between the blood glucose estimated from the model and the real blood glucose measured by the sensor over the past observation period;
 c) determining the duration of a prediction period to come, taking into account the value of said at least one numerical indicator, the duration of the prediction period to come being selected to be all the shorter as the error between the blood glucose estimated from the model and the real blood glucose measured by the sensor over the past observation period is significant, and conversely; and
 d) predicting, based on the physiological model, the future evolution of the patient's blood glucose over the prediction period to come, and controlling the insulin injection device by taking the prediction into account.

According to an embodiment, the numerical indicator comprises the standard deviation between the blood glucose estimated from the model and the real blood glucose measured by the sensor during the past observation period.

According to an embodiment, the numerical indicator comprises the difference between the real blood glucose measured by the sensor and the blood glucose estimated by the model at a given time.

According to an embodiment, the numerical indicator comprises the difference between the derivative of the real blood glucose measured by the sensor and the derivative of the blood glucose estimated by the model at a given time.

According to an embodiment, the processing and control unit is configured to, at step c), compare the value of the numerical indicator with first thresholds, and select the duration of the prediction period from among a plurality of predefined durations according to the result of the comparison.

According to an embodiment, the processing and control unit is further capable, after step b), of determining, from the value of the numerical indicator, whether the model is sufficiently reliable to be used as a basis for the control of the insulin injection device and, in the opposite case, of controlling the insulin injection device according to a substitute method, without taking into account the prediction made based on the model.

According to an embodiment, to determine whether the model is sufficiently reliable, the processing and control unit compares the value of the numerical indicator with a second threshold.

According to an embodiment, the processing and control unit is capable of determining and of automatically adjusting the second threshold from past data measured on the patient, so that the control of the insulin injection device is based on the predictions made by the model at least for a certain percentage P of the time.

According to an embodiment, the substitute method is a predictive control method based on a simplified physiological model.

According to an embodiment, the substitute method comprises controlling the insulin injection device to deliver preprogrammed insulin doses corresponding to a reference basal rate prescribed to the patient.

According to an embodiment, the substitute method comprises controlling the insulin injection device to deliver insulin doses determined by the processing and control unit according to the current blood glucose level measured by the sensor and/or to the variation speed of the blood glucose measured by the sensor.

BRIEF DESCRIPTION OF THE DRAWINGS

The foregoing and other features and advantages will be discussed in detail in the following non-limiting description of specific embodiments in connection with the accompanying drawings, in which.

DETAILED DESCRIPTION

Figure 1:
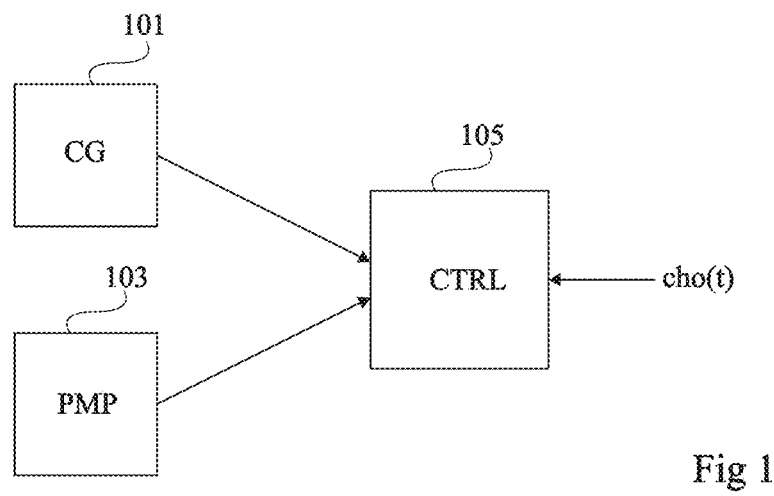
FIG. 1 schematically shows, in the form of blocks, an embodiment of an automated system for regulating a patient's blood glucose.

The same elements have been designated with the same reference numerals in the different drawings. For clarity, only those elements which are useful to the understanding of the described embodiments have been shown and are detailed. In particular, the blood glucose measurement device and the insulin injection device of the described regulation system have not been detailed, the described embodiments being compatible with all or part of known blood glucose measurement and insulin injection devices. Further, the hardware implementation of the processing and control unit of the described regulation system has not been detailed, the forming of such a processing and control unit being within the abilities of those skilled in the art based on the functional indications of the present disclosure.

FIG. 1 schematically shows in the form of blocks an embodiment of an automated system of regulation of a patient's blood glucose.

The system of FIG. 1 comprises a sensor 101 (CG) capable of measuring the patient's blood glucose. In normal operation, sensor 101 may be permanently positioned on or in the patient's body, for example, at the level of his/her abdomen. Sensor 101 is for example a CGM-type ("Continuous Glucose Monitoring") sensor, that is, a sensor capable of continuously measuring (for example, at least once every five minutes) the patient's blood glucose. Sensor 101 is for example a subcutaneous blood glucose sensor.

The system of FIG. 1 further comprises an insulin injection device 103 (PMP), for example, a subcutaneous injection device. Device 103 is for example, an automatic injection device of insulin pump type, comprising an insulin reservoir connected to an injection needle implanted under the patient's skin, and the pump may be electrically controlled to automatically inject determined insulin doses at determined times. In normal operation, injection device 103 may be permanently positioned inside of or on the patient's body, for example, at the level of his/her abdomen.

The system of FIG. 1 further comprises a processing and control unit 105 (CTRL) connected on the one hand to blood glucose sensor 101, for example, by a wire link or by a radio (wireless) link, and on the other hand to injection device 103, for example, by wire or radio link. In operation, processing and control unit 105 is capable of receiving the data relative to the patient's blood glucose measured by sensor 101, and of electrically controlling device 103 to inject to the patient determined insulin doses at determined times. In this example, processing and control unit 105 is further capable of receiving, via a user interface, not detailed, data cho(t) representative of the time variation of the quantity of glucose ingested by the patient. The user interface may further be provided to enable to input additional information capable of easing the blood glucose regulation, for example, information relative to the patient's physical activity, or also to his/her stress, or any other information relative to the patient's metabolism, or also the types of food ingested by the patient (fatty or not, for example).

Processing and control unit 105 is capable of determining the insulin doses to be injected to the patient by taking into account, in particular, the history of the blood glucose measured by sensor 101, the history of the insulin injected by device 103, and the history of glucose ingestion by the patient. To achieve this, processing and control unit 105 comprises a digital calculation circuit (not detailed), for example comprising a microprocessor. Processing and control unit 105 is for example a mobile device carried by the patient all along the day and/or the night, for example, a smart phone-type device configured to implement a regulation method of the type described hereafter.

In the embodiment of FIG. 1, processing and control unit 105 is capable of determining the quantity of insulin to be delivered to the patient by taking into account a prediction of the future evolution of his/her blood glucose over time. More particularly, processing and control unit 105 is capable, based on the injected insulin history and on the ingested blood glucose history (as well as on the above-mentioned possible additional information), and based on a physiological model describing the assimilation of insulin by the patient's body and its impact on the blood glucose, of determining a curve representative of the expected evolution of the patient's blood glucose over time, over a period to come, for example, a period from 1 to 10 hours. Taking this curve into account, processing and control unit 105 determines the insulin doses that should be injected to the patient during the prediction period to come, so that the patient's real blood glucose (as opposed to the blood glucose estimated based on the physiological model) remains within acceptable limits, and in particular to limit risks of hyperglycemia or of hypoglycemia. In such an operating mode, as will be explained in further detail hereafter, the data relative to the real blood glucose measured by sensor 101 are mainly used for purposes of calibration of the physiological model.

Figure 2:
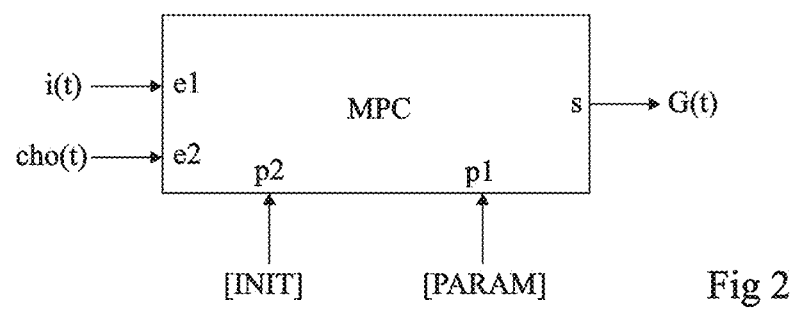
FIG. 2 is a simplified representation of a physiological model used in the system of FIG. 1 to predict the future evolution of the patient's blood glucose.

FIG. 2 is a simplified representation of a MPC physiological model used in the system of FIG. 1 to predict the future evolution of the patient's blood glucose. In FIG. 2, the model is shown in the form of a processing block comprising:

an input e1 having a signal i(t) representative of the evolution, over time t, of the quantity of insulin injected to the patient, applied thereto;

an input e2 having a signal cho(t) representative of the evolution, over time t, of the quantity of glucose ingested by the patient, applied thereto; and an output s delivering a signal G(t) representative of the evolution, over time t, of the patient's blood glucose.

The MPC physiological model is for example a compartmental model comprising, in addition to input variables i(t) and cho(t) and output variable G(t), a plurality of state variables corresponding to physiological variables of the patient, varying over time. The time variation of the state variables and of the output variable G(t) is ruled by a differential equation system comprising a plurality of parameters represented in FIG. 2 by a vector [PARAM] applied to an input p1 of the MPC block. The response of the physiological model is further conditioned by the initial states or initial values assigned to the state variables, represented in FIG. 2 by a vector [INIT] applied to an input p2 of the MPC block.

As an example, the MPC physiological model used in the system of FIG. 1 is the model called Hovorka model, described in the article entitled "Nonlinear model predictive control of glucose concentration in subjects with type 1 diabetes" of Roman Hovorka et al. (Physiol Meas. 2004; 25:905-920), and in the article entitled "Partitioning glucose distribution/transport, disposal, and endogenous production during IVGTT", of Roman Hovorka et al. (Am J Physiol Endocrinol Metab 282: E992-E1007, 2002). More generally, any other physiological model describing the assimilation of insulin by a patient's body and its effect on the patient's blood glucose may be used, for example, the model called Cobelli's model, described in the article entitled "A System Model of Oral Glucose Absorption: Validation on Gold Standard Data", of Chiara Dalla Man et al. (IEEE TRANSACTIONS ON BIOMEDICAL ENGINEERING, VOL. 53, No. 12, December 2006).

Among the parameters of vector [PARAM], some may be considered as constant for a given patient. Other parameters, called time-dependent parameters hereafter, are however capable of varying over time. Due to this variability of certain parameters of the system, it is in practice necessary to regularly recalibrate the model used, for example, every 1 to 20 minutes, for example, every 5 minutes, to make sure that the predictions of the model remain relevant. Such an update of the model, called model personalization, should be capable of being automatically carried out by the system of FIG. 1, that is, without requiring physically measuring the time-dependent parameters of the system on the patient and then transmitting them to processing and control unit 105.

Figure 3:
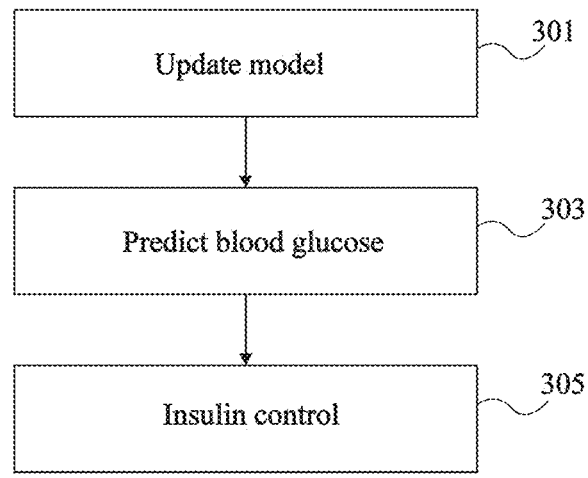
FIG. 3 is a diagram illustrating an example of an automated insulin regulation method capable of being implemented by the system of FIG. 1.

FIG. 3 is a diagram illustrating an example of an automated glucose regulation method capable of being implemented by the system of FIG. 1.

This method comprises a step 301 of recalibration or update of the model, which may for example be repeated at regular intervals, for example, every 1 to 20 minutes. During this step, processing and control unit 105 implements a method of re-estimation of the time-dependent parameters of the model, taking into account the data relative to the insulin effectively injected by device 103 and the data relative to the real blood glucose measured by sensor 101 for a past observation period of duration $\Delta T$, for example a period from 1 to 10 hours preceding the calibration step. More particularly, during the calibration step, processing and control unit 105 simulates the patient's behavior over the past observation period based on the physiological model (taking into account possible glucose ingestions and insulin injections during this period) and compares the curve of the blood glucose estimated by the model with the curve of the real blood glucose measured by the sensor during this same period. Processing and control unit 105 then searches, for the time-dependent parameters of the model, a set of values leading to minimizing a quantity representative of the error between the curve of the blood glucose estimated by the model and the curve of the real blood glucose measured by the sensor during the observation period. As an example, the processing and control unit searches for a set of parameters leading to minimizing an indicator m representative of the area between the curve of the blood glucose estimated by the model and the curve of the real blood glucose measured by the sensor during the observation period, also called standard deviation between the estimated glucose and the real glucose, for example defined as follows:

$$m = \frac{1}{\Delta T} \sum_{t=t_0-\Delta T}^{t_0} |g(t) - \hat{g}(t)|^2$$

where t is the discretized time variable, $t_0-\Delta T$ corresponds to the time of beginning of the past observation phase, $t_0$ corresponds to the end time of the past observation phase (for example corresponding to the time of beginning of the model calibration step), g is the curve of time variation of the real blood glucose measured by sensor 101 during period $[t_0-\Delta T, t_0]$, and $\hat{g}$ is the curve of the blood glucose estimated based on the model during period $[t_0-\Delta T, t_0]$. As a variation, for the calculation of the standard deviation, variable $\Delta T$ may be replaced with the number of measurements performed during the past observation period. The optimal parameter search algorithm used during this step is not detailed in the present application, the described embodiments being compatible with usual algorithms used in various field to solve problems of parameter optimization by minimization of a cost function.

It should be noted that during step 301, in addition to the time-dependent parameters of the model, processing and control unit 105 defines a vector [INIT] of initial states (states at time $t_0-\Delta T$) of the state variables of the model, to be able to simulate the patient's behavior from the model. To define the initial states of the state variables of the model, a first possibility comprises making the assumption that, in the period preceding the observation period $[t_0-\Delta T, t_0]$ having the model calibration based thereon, the patient was in a stationary state, with a constant injected insulin flow, and no dietary intake of glucose. Under this assumption, all the derivatives of the differential equation system may be considered as zero at initial time $t_0-\Delta T$. The values at time $t_0-\Delta T$ of the state variables of the system may then be analytically calculated. To improve the initialization, another possibility comprises making the same assumptions as previously, while adding the constraint for the blood glucose estimated at time $t_0-\Delta T$ to be equal to the real blood glucose measured by the sensor. To further improve the initialization, another possibility is to consider the initial states of the state variables of the model as random variables, just as the time-dependent parameters of the model. The initial states of the state variables are then determined in the same way as the time-dependent parameters of the model, that is, processing and control unit 105 searches for a set of values of initial states [INIT] resulting in minimizing a quantity representative of the error between the curve of the blood glucose estimated by the model and the curve of the real blood glucose during the past observation period.

The method of FIG. 3 further comprises, after step 301, a step 303 of prediction, by processing and control unit 105, of the time variation of the patient's blood glucose over a prediction period to come $[t0, t_0+T_{pred}]$ of duration $T_{pred}$, for example, in the range from 1 to 10 hours, based on the physiological model updated at step 301 and taking into account the history of the insulin injected to the patient and the history of the glucose ingested by the patient.

The method of FIG. 3 further comprises, after step 303, a step 305 of determination, by processing and control unit 105, taking into account the curve of the future blood glucose predicted at step 303, of the insulin doses to be injected to the patient for the prediction period to come $[t0, t_0+T_{pred}]$. At the end of this step, processing and control unit 105 may program injection device 103 to deliver the doses determined during the prediction period $[t0, t_0+T_{pred}]$.

Steps 303 of prediction of the blood glucose and 305 of determination of the future doses of insulin to be delivered may for example be repeated at each update of the physiological model (that is, after each iteration of step 301), for each new glucose ingestion notified by the patient, and/or for each new administration of an insulin dose by injection device 103.

In the above-mentioned method, duration $T_{pred}$ of the period of prediction of the future evolution of the patient's blood glucose is an important parameter, conditioning the performance of the regulation system. Given the relatively slow dynamics of the system which is desired to regulated, it would be desirable for the prediction period $T_{pred}$ to be relatively long, for example, in the order of 4 hours or more, to be able to anticipate and estimate at best the patient's insulin needs. However, in practice, the imperfections of the model used force to limit the considered prediction horizon.

According to an aspect of an embodiment, processing and control unit 105 is capable, after each update of the physiological model (step 301), of calculating one or a plurality of numerical indicators representative of the reliability of the updated model, and of adjusting the prediction duration $T_{pred}$ according to the indicators. More particularly, if the updated model is considered reliable, prediction duration $T_{pred}$ will be selected to be relatively long and, if the model is considered little reliable, prediction duration $T_{pred}$ will be selected to be relatively short. As compared with a system where prediction duration $T_{pred}$ is fixed, an advantage of such an operating mode is that it enables to improve the quality of the prediction of the patient's future blood glucose, and thus to more relevantly control insulin intakes.

Figure 4:
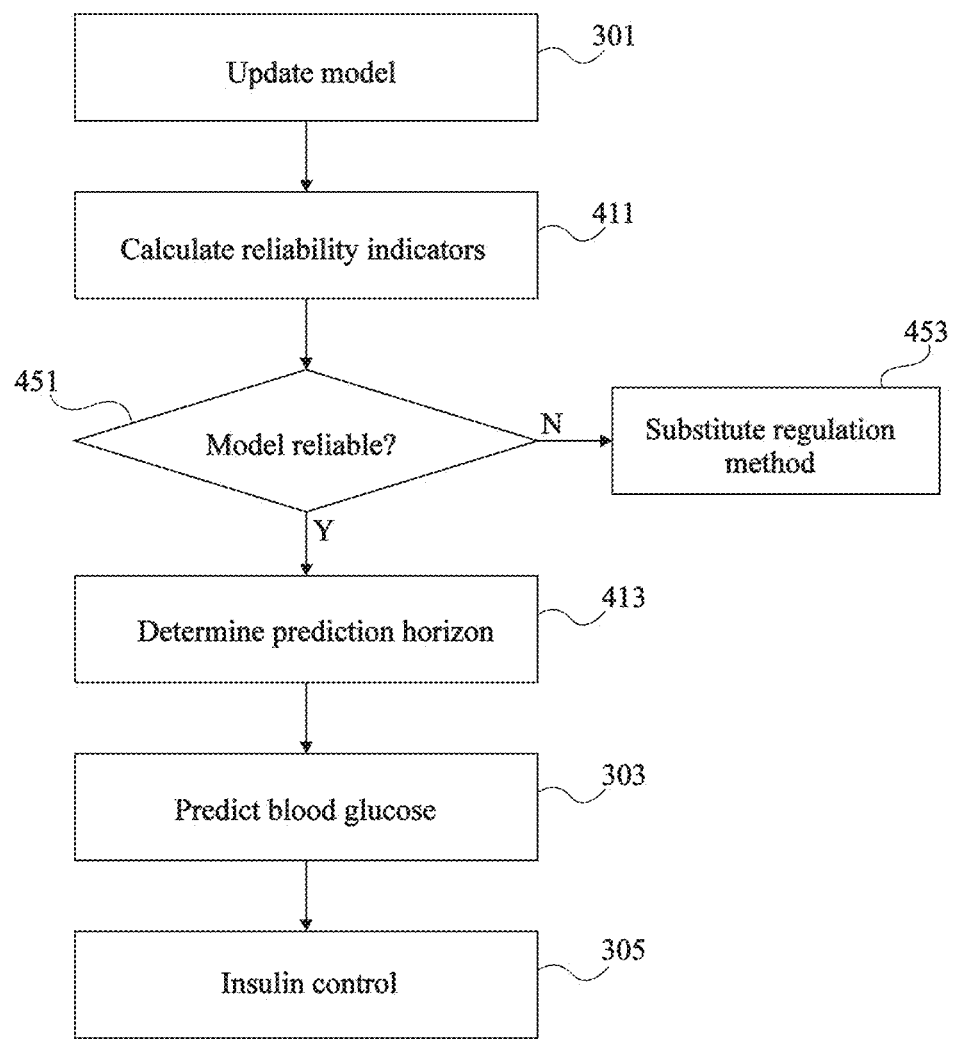
FIG. 4 is a diagram illustrating in further detail an embodiment of an automated blood glucose regulation method implemented by the system of FIG. 1.

FIG. 4 is a diagram illustrating in further detail an example of an automated blood glucose regulation method implemented by the system of FIG. 1, wherein prediction duration $T_{pred}$ is adjusted according to an estimate of the reliability of the physiological model.

This method comprises the same steps 301, 303, and 305 as in the example of FIG. 3. However, the method of FIG. 4 further comprises, after each step 301 of update of the physiological model and before the implementation of the next steps 303 of prediction of the patient's future blood glucose and 305 of control of the insulin delivery based on the blood glucose prediction, a step 411 of calculation of one or a plurality of numerical indicators of the reliability of the updated model, and a step 413 of adjustment of prediction duration $T_{pred}$ according to the reliability indicators calculated at step 411.

During step 411, processing and control unit 105 calculates one or a plurality of numerical indicators representative of the reliability of the model updated at step 301. As an example, the processing and control unit calculates three numerical reliability indicators MM, GD, and SD. Indicator MM corresponds to the standard deviation between the blood glucose estimated from the updated model and the curve of the real blood glucose measured by sensor 101 during a past observation period, for example, a period from 1 to 10 hours preceding time to, for example, period [$t_0$-$\Delta T$, $t_0$]. Indicator GD corresponds to the difference between the real blood glucose measured by sensor 101 and the blood glucose estimated by the updated model at a given time, for example, at time $t_0$, and indicator SD corresponds to the difference between the slope or derivative of the real blood glucose measured by sensor 101 and the slope or derivative of the blood glucose estimated by the updated model at a given time, for example, at time $t_0$.

During step 413, the processing and control unit determines, based on the numerical reliability indicator(s) calculated at step 411, the prediction duration $T_{pred}$ to be used for the implementation of step 303. As an example, prediction duration $T_{pred}$ is selected among n decreasing predefined values $D1, \ldots, Dn$, n being an integer greater than or equal to 2, according to the value of the numerical reliability indicators calculated at step 411. As an example, for each of the m reliability indicators $I_j$ calculated at step 411, j being an integer varying from 1 to m and m being an integer greater than or equal to 1, the value of the indicator is compared with a set of n predefined thresholds $SI_{j1}, \ldots, SI_{jn}$ with increasing values. Processing and control unit 105 then searches for the smallest threshold index k such that, for each of the m indicators $I_j$ calculated at step 411, the value of indicator $I_j$ is smaller than threshold $SI_{jk}$. Prediction horizon $T_{pred}$ then is selected to be equal to duration Dk. Thus, duration $T_{pred}$ of the prediction period to come is selected to be all the shorter as the error between the blood glucose estimated from the model and the real blood glucose measured by the sensor over the past observation period is significant, and conversely. In other words, duration $T_{pred}$ of the prediction period to come is a decreasing function of the error between the blood glucose estimated from the model and the real blood glucose measured by the sensor over the past observation period, it being understood that a decreasing function here means a function which may be decreasing continuously or stepwise. More generally, according to the desired object, other functions and/or decision rules enabling to determine prediction duration $T_{pred}$ based on the reliability indicators calculated at step 411 may be implemented.

After step 413, steps 303 and 305 may be implemented similarly to what has been previously described.

It should be noted that in certain cases, the reliability of the physiological model updated at step 301 may be so low that it is preferable to stop using the model to regulate the patient's blood glucose.

In the example of FIG. 4, the control and processing unit 105 of the regulation system is further capable, after each update or recalibration of the physiological model (step 301), based on the reliability indicators calculated at step 411, of determining whether the updated model is sufficiently reliable to be used to regulate the patient's blood glucose.

More particularly, the method of FIG. 4 comprises, between steps 411 and 413, a step 451 of verification of the reliability of the model updated at step 301. As an example, the reliability of the model may be considered as sufficient by processing and control unit 105 when the values of the indicators calculated at step 411 are smaller than predefined thresholds, and insufficient in the opposite case. As an example, taking the above-defined notations, the reliability of the model may be considered as sufficient by processing and control unit 105 when for each of the m reliability indicators $I_j$ calculated at step 411, the value of the indicator is smaller than the corresponding threshold $SI_{jn}$, and insufficient when for at least one of indicators $I_j$, the value of the indicator is greater than the corresponding threshold $SI_{jn}$. More generally, any other quality criterion or any other combination of quality criteria may be used at step 451 to determine whether the physiological model recalibrated at step 301 is sufficiently reliable.

If the physiological model is considered as sufficiently reliable at step 451 (O), steps 413, 303, and 305 can be implemented similarly to what has been previously described, that is, processing and control unit 105 continues following the predictions made by the physiological model to regulate the administration of insulin to the patient, by adjusting the prediction horizon $T_{pred}$ according to the degree of reliability of the model.

If the physiological model is considered to be insufficiently reliable at step 451 (N), processing and control unit 105 stops using this model to regulate the delivery of insulin to the patient and implements a substitute regulation method at a step 453.

As an example, at step 453, processing and control unit 105 uses a simplified physiological model, for example, a compartmental model comprising a small number of state variables and number of parameters as compared with the initial model, to predict the evolution of the patient's blood glucose and accordingly regulate the insulin injection.

As a variation, at step 453, processing and control unit 105 stops implementing a predictive control, that is, it stops using a physiological model to predict the patient's future blood glucose and accordingly regulate the insulin injection. In this case, processing and control unit 105 for example controls insulin injection device 103 to deliver preprogrammed insulin doses, for example corresponding to a reference basal rate prescribed to the patient. As a variation, processing and control unit 105 uses an algorithm of decision matrix type to determine the insulin doses to be delivered to the patient, according to various observed parameters such as the current blood glucose level measured by sensor 101, or also the blood glucose variation speed (or slope) over a past period.

Such a substitute method may for example be used during a predetermined time period. At the end of this period, steps 301 of calibration of the main physiological model, 411 of calculation of the reliability indicator(s) of the main physiological model, and 451 of estimation of the quality of the main physiological model may be repeated to, if the quality of the main physiological model is considered sufficient, reactivate the use of the main model to regulate the delivery of insulin to the patient.

As an example, the thresholds used at step 451 to determine whether the main physiological model is sufficiently reliable to be used are selected to maximize the probability for the regulation system to operate for at least a certain percentage P of the time, for example, at least 70% of the time, based on the main physiological model.

The thresholds used at steps 451 and 413 are for example determined based on an analysis of past data measured over a sample of a plurality of patients. As an example, the regulation algorithm may be replayed for a plurality of patients on a test bench and, for each patient, at each update of the physiological model, for each of the n possible values D1, . . . , Dn of prediction duration $T_{pred}$, the standard deviation, over prediction period $T_{pred}$, between the blood glucose estimated from the updated model and the curve of the real blood glucose measured by sensor 101 may be calculated. At each update of the model, the m reliability indicators of the updated model $I_1, \ldots, I_m$ are further calculated. Thus, at each update of the model, a set of m values corresponding to the reliability indicators of the model such as defined hereabove and a set of n values corresponding to effective measurements of the reliability of the model for the n considered prediction durations D1, . . . , Dn, are available. The study of the correlations between the reliability indicators of the model and the effective reliability measurements enables to determine the thresholds to be used at step 413 to select the duration of the prediction period after each update of the model, and/or at step 451 to decide whether or not it is appropriate to switch to a substitute regulation method. The determination of the thresholds based on the above-mentioned values of reliability indicators and of effective reliability measurements may be totally or partially automated.

As a variation, the thresholds used at steps 451 and 413 are determined similarly to what has just been described, but only based on the past data measured on the patient using the system, which enables to personalize the operation of the regulation system. In this case, processing and control unit 105 may be configured to regularly recalculate the thresholds used at step 413 and/or at step 451, taking into account the new data measured on the patient since the last update of the thresholds.

The invention claimed is:

1. An automated system for regulation of a patient's blood glucose, comprising:
   a blood glucose sensor;
   an insulin injection device; and
   a processing and control unit,
   wherein the processing and control unit is capable of:
   a) implementing, taking into account a real blood glucose measured by the sensor during a past observation period, a step of automated calibration of a physiological model capable of predicting evolution of the patient's blood glucose;
   b) at an end of the step of automated calibration, calculating at least one numerical indicator representative of an error between a blood glucose estimated from the model and the real blood glucose measured by the sensor over the past observation period;
   c) determining a duration of a prediction period to come, taking into account a value of said at least one numerical indicator, the duration of the prediction period to come being selected to be shorter as the error between the blood glucose estimated from the model and the real blood glucose measured by the sensor over the past observation period is larger; and
   d) predicting, from the physiological model, a future evolution of the patient's blood glucose over the prediction period to come, and controlling the insulin injection device by taking into account a prediction obtained from the predicting.

2. The system of claim 1, wherein said at least one numerical indicator comprises a standard deviation between the blood glucose estimated from the model and the real blood glucose measured by the sensor during the past observation period.

3. The system of claim 1, wherein said at least one numerical indicator comprises a difference between the real blood glucose measured by the sensor and the blood glucose estimated by the model at a given time.

4. The system of claim 1, wherein said at least one numerical indicator comprises a difference between a derivative of the real blood glucose measured by the sensor and a derivative of the blood glucose estimated by the model at a given time.

5. The system of claim 1, wherein the processing and control unit is configured to, at step c), compare the value of said at least one numerical indicator with first thresholds, and select the duration of the prediction period from among a plurality of predefined durations according to a result of the comparing.

6. The system of claim 1, wherein the processing and control unit is further capable, after step b), of determining, based on the value of said at least one numerical indicator, whether the model is sufficiently reliable to be used as a basis for the controlling of the insulin injection device and, in a case where the model is insufficiently reliable, of controlling the insulin injection device according to a substitute method, without taking into account the prediction obtained from the predicting from the physiological model.

7. The system of claim 6, wherein the processing and control unit is configured to, in order to determine whether the model is sufficiently reliable, compare the value of said at least one numerical indicator with a second threshold.

8. The system of claim 7, wherein the processing and control unit is capable of determining and of automatically adjusting the second threshold from past data measured on the patient, so that the controlling of the insulin injection device is based on predictions made by the model at least for a certain percentage of the time.

9. The system of claim 6, wherein the substitute method is a predictive control method based on a simplified physiological model.

10. The system of claim 6, wherein the substitute method comprises controlling the insulin injection device to deliver preprogrammed insulin doses corresponding to a reference basal rate prescribed to the patient.

11. The system of claim 6, wherein the substitute method comprises controlling the insulin injection device to deliver insulin doses determined by the processing and control unit according to a current blood glucose level measured by the sensor and/or to the variation speed of the blood glucose measured by the sensor.

\* \* \* \* \*